US008658799B2

(12) United States Patent
Bohlin et al.

(10) Patent No.: US 8,658,799 B2
(45) Date of Patent: Feb. 25, 2014

(54) PROCESS FOR THE PREPARATION OF CRYSTALLINE MODIFICATIONS FOR USE IN THE PREPARATION OF ESOMEPERAZOLE SODIUM SALT

(75) Inventors: Martin Bohlin, Södertälje (SE); Ursula Noreland, Södertälje (SE)

(73) Assignee: Astrazeneca AB, Sodertalje (SE)

( * ) Notice: Subject to any disclaimer, the term of this patent is extended or adjusted under 35 U.S.C. 154(b) by 1587 days.

(21) Appl. No.: 11/570,717

(22) PCT Filed: Jun. 20, 2005

(86) PCT No.: PCT/SE2005/000954
§ 371 (c)(1),
(2), (4) Date: Dec. 15, 2006

(87) PCT Pub. No.: WO2006/001753
PCT Pub. Date: Jan. 5, 2006

(65) Prior Publication Data
US 2008/0039503 A1 Feb. 14, 2008

Related U.S. Application Data

(60) Provisional application No. 60/582,617, filed on Jun. 24, 2004.

(51) Int. Cl.
*C07D 401/12* (2006.01)
*A61K 31/4439* (2006.01)

(52) U.S. Cl.
USPC ..................................... 546/273.7; 514/338

(58) Field of Classification Search
USPC ....................................... 514/338; 546/273.7
See application file for complete search history.

(56) References Cited

U.S. PATENT DOCUMENTS

| 4,378,974 | A |   | 4/1983  | Petit et al.           |         |
|-----------|---|---|---------|------------------------|---------|
| 5,693,818 | A |   | 12/1997 | Von Unge               |         |
| 5,714,504 | A |   | 2/1998  | Lindberg et al.        |         |
| 5,948,789 | A |   | 9/1999  | Larsson et al.         |         |
| 6,162,816 | A | * | 12/2000 | Bohlin et al. .......... | 514/338 |
| 6,207,188 | B1 |  | 3/2001  | Gustavsson et al.      |         |
| 6,369,085 | B1 |  | 4/2002  | Cotton et al.          |         |
| 6,511,996 | B1 | * | 1/2003 | Nilsson ............... | 514/338 |
| 6,875,872 | B1 |  | 4/2005  | Lindberg et al.        |         |

FOREIGN PATENT DOCUMENTS

| EP | 0124495 | 1/1987  |
|----|---------|---------|
| EP | 0533264 | 11/1999 |
| EP | 1206466 | 10/2005 |
| EP | 1306375 | 10/2006 |

(Continued)

OTHER PUBLICATIONS

Muzaffar et al. "Polymorphism and drug availability" J. Phar. 1(1) 59-66 (1979).*

(Continued)

*Primary Examiner* — Celia Chang
(74) *Attorney, Agent, or Firm* — Astrazeneca Pharmaceuticals LP

(57) ABSTRACT

The present invention relates to a new process for the preparation of crystal modifications for use in the preparation of esomeprazole sodium salt. Further, the present invention also relates to the use of the new crystal modifications for the treatment of gastrointestinal disorders, pharmaceutical compositions containing them as well as the crystal modifications, as such.

7 Claims, 5 Drawing Sheets

*An X-ray powder diffractogram of esomeprazole sodim salt modification C measured with variable slits.*

(56) References Cited

FOREIGN PATENT DOCUMENTS

| | | |
|---|---|---|
| WO | 9427988 | 12/1994 |
| WO | 9602535 | 2/1996 |
| WO | 9828294 | 7/1998 |
| WO | 9854171 | 12/1998 |
| WO | 9900380 | 1/1999 |
| WO | 9927988 | 6/1999 |
| WO | 03089408 | 10/2003 |
| WO | 2004002982 | 1/2004 |
| WO | 2004037253 | 5/2004 |
| WO | WO-2004-089935 | 10/2004 |
| WO | WO-2004-111029 | 12/2004 |

OTHER PUBLICATIONS

Jain et al. "Polymorphisom in pharmacey" Indian Drugs 23(g)315-329 (1986).*

Doelker et al. "Crystalline modification . . . " CA 138:209993 (2002).*

Doelker et al. "Physicochemical behavior or active . . . " CA 132:325872 (2000).*

Otsuka et al. "effect of polymorphic . . . " Chem. Pharm. Bull, 47(6) 852-856 (1999).*

Kirk_othmer "Encyclopedia of Chemical Technology" vo. 8, p. 95-147 (2002).*

\* cited by examiner

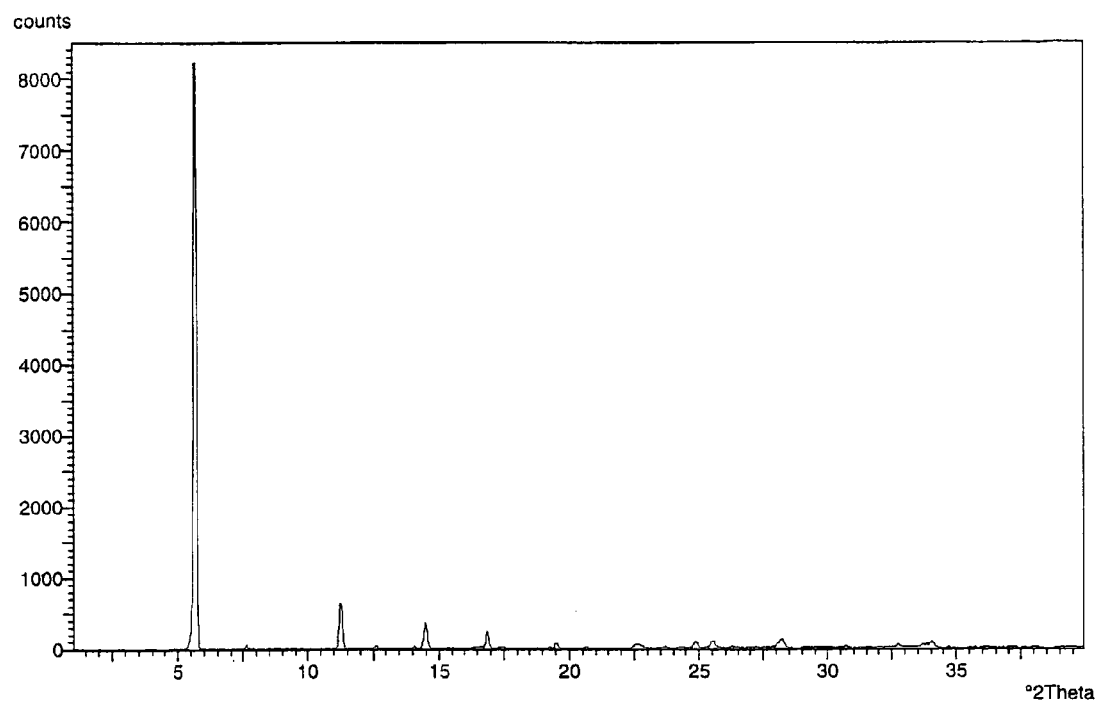
*Figure 1.* An X-ray powder diffractogram of esomeprazole sodim salt modification C measured with variable slits.

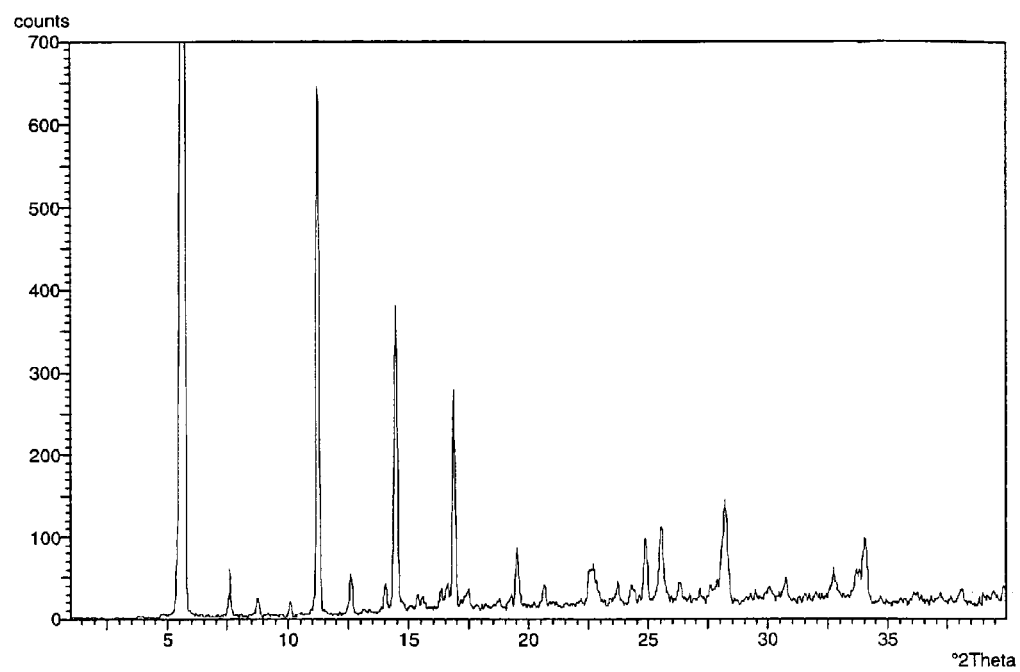
Figure 2. An X-ray powder diffractogram of esomeprazole sodim salt modification C measured with variable slits, zoom-in version of Figure 1.

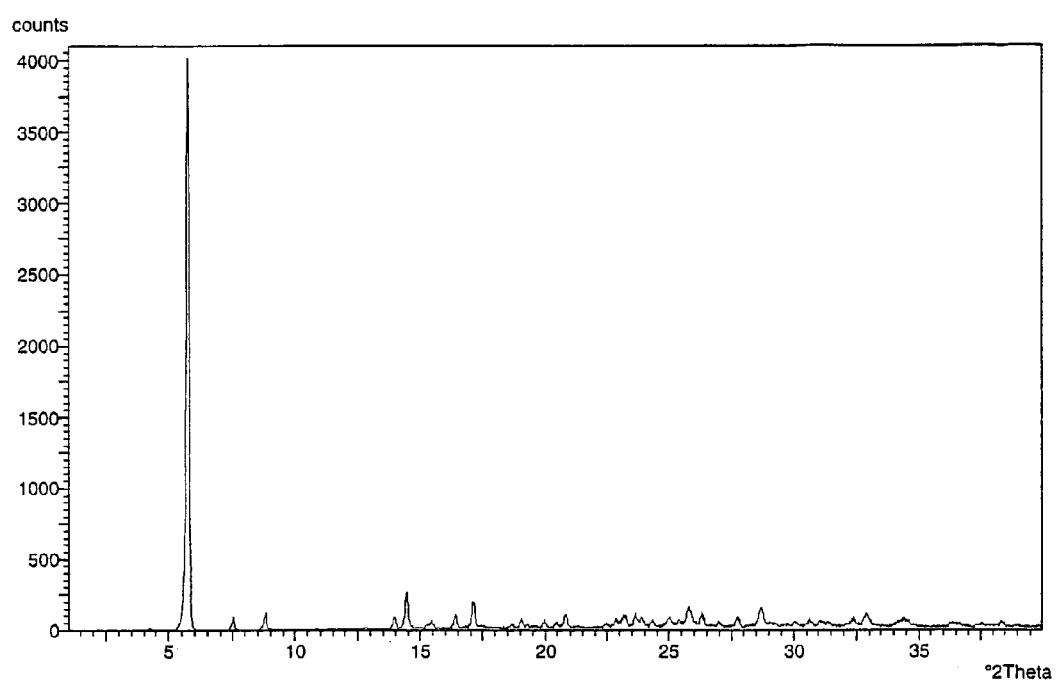
*Figure 3.* An X-ray powder diffractogram of esomeprazole sodim salt modification E measured with variable slits.

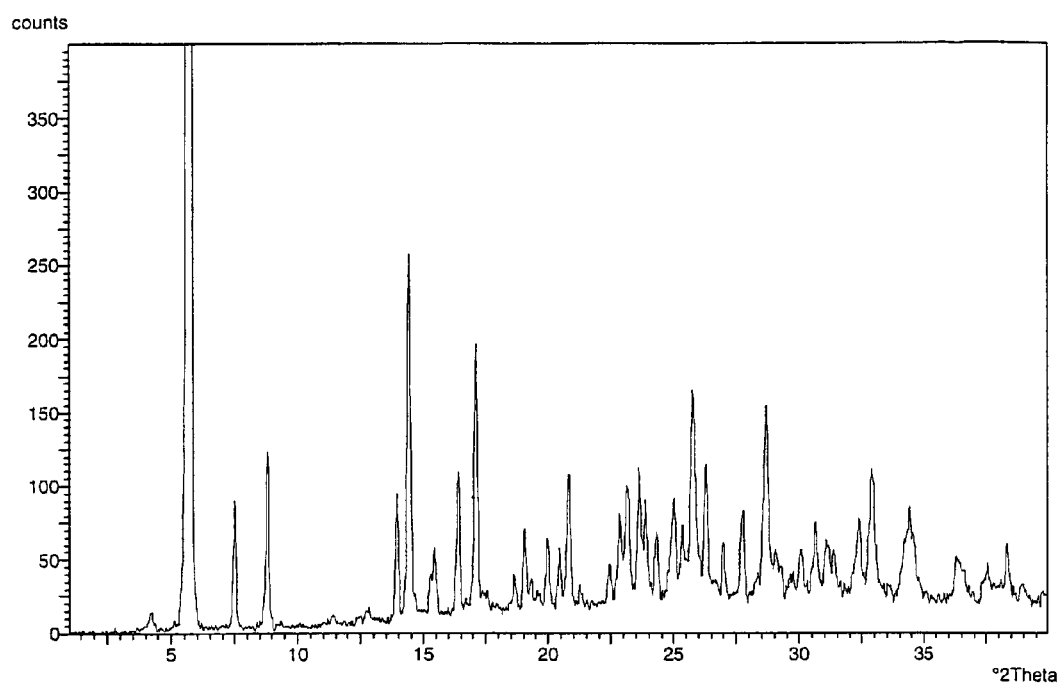
Figure 4. An X-ray powder diffractogram of esomeprazole sodim salt modification E measured with variable slits, zoom-in version of Figure 3.

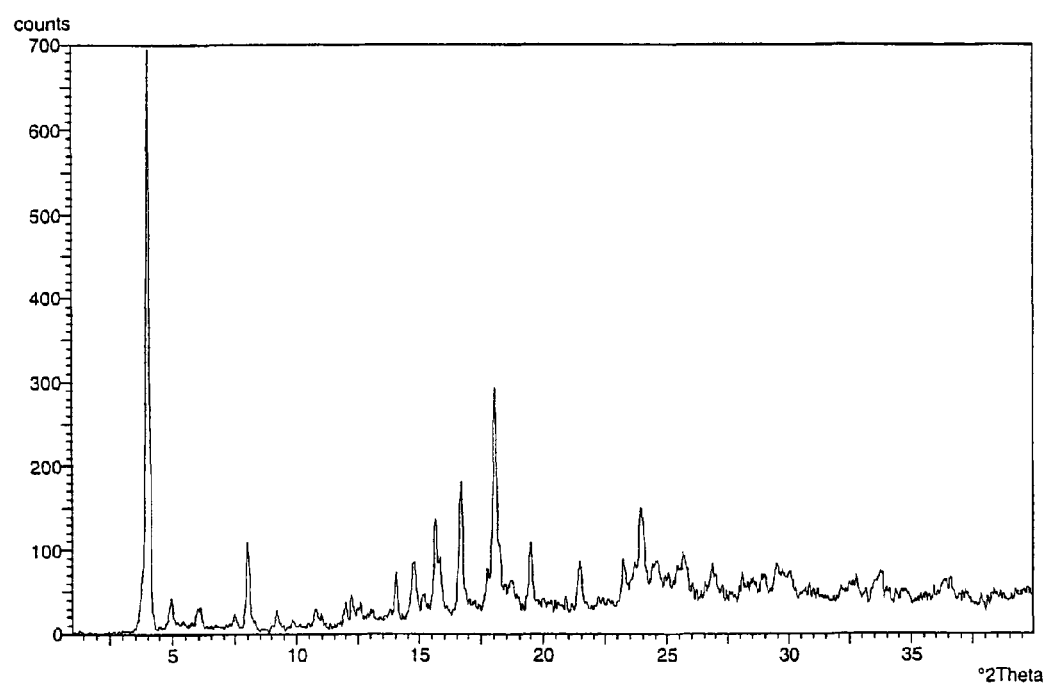
*Figure 5.* An X-ray powder diffractogram of esomeprazole sodim salt modification H measured with variable slits.

PROCESS FOR THE PREPARATION OF CRYSTALLINE MODIFICATIONS FOR USE IN THE PREPARATION OF ESOMEPERAZOLE SODIUM SALT

This application is the U.S. national stage of PCT/SE2005/000954, filed on Jun. 20, 2005, which claims priority to U.S. provisional patent application serial no. 60/582,617, filed on Jun. 24, 2004.

FIELD OF THE INVENTION

The present invention relates to a new process for the preparation of crystal modifications for use in the preparation of esomeprazole sodium salt. Further, the present invention also relates to the use of the new crystal modifications for the treatment of gastrointestinal disorders, pharmaceutical compositions containing them as well as the crystal modifications, as such.

BACKGROUND OF THE INVENTION AND PRIOR ART

Omeprazole, i.e. the compound 5-methoxy-2-[[(4-methoxy-3,5-dimethyl-2-pyridinyl)methyl]sulfinyl]-1H-benzimidazole, and therapeutically acceptable salts thereof, are described in EP 5129. Some specific alkaline salts of omeprazole are disclosed in EP 124 495.

Omeprazole is a sulfoxide and a chiral compound, wherein the sulfur atom is the stereogenic center. Thus, omeprazole is a racemic mixture of its two single enantiomers, the R— and S-enantiomer of omeprazole, the latter having the generic name esomeprazole. Esomeprazole is recently launched as a new generation of proton pump inhibitors, wherein the active pharmaceutical ingredient is esomeprazole magnesium salt. Esomeprazole shows improvements in the treatment of GERD compared to previous medications.

The absolute configurations of the enantiomers of omeprazole have been determined by an X-ray study of an N-alkylated derivative of the (+)-enantiomer in non-salt form. The (+)-enantiomer of the non-salt form and the (−)-enantiomer of the non-salt form were found to have R and S configuration, respectively, and the (+)-enantiomer of the magnesium salt and the (−)-enantiomer of the magnesium salt were also found to have R and S configuration, respectively. The conditions for the optical rotation measurement for each of these enantiomers are described in WO 94/27988.

Certain salts of single enantiomers of omeprazole and their preparation are disclosed in WO 94/27988. These compounds have improved pharmacokinetic and metabolic properties, which will give an improved therapeutic profile such as a lower degree of interindividual variation.

WO 96/02535 discloses a process for the preparation of the single enantiomers of omeprazole and salts thereof, including a sodium salt.

WO 98/54171 discloses a process for the preparation of the magnesium salt of the S-enantiomer of omeprazole trihydrate, wherein a potassium salt of S-omeprazole is used as an intermediate.

WO 00/44744 discloses a potassium salt of S-omeprazole free from methanol. WO 03/089408 (Sun Pharmaceutical Industries Limited) discloses alkali or alkaline earth metal salts of esomeprazole, including a sodium salt.

BRIEF DESCRIPTION OF THE DRAWINGS

FIG. 1 is an X-ray powder diffractogram of esomeprazole sodium salt modification C.

FIG. 2 is a zoom-in version of FIG. 1.
FIG. 3 is an X-ray powder diffractogram of esomeprazole sodium salt modification E.
FIG. 4 is zoom-in version of FIG. 3.
FIG. 5 is an X-ray powder diffractogram of esomeprazole sodium salt modification H.

DESCRIPTION OF THE INVENTION

It has surprisingly been found that during the preparation of esomeprazole sodium salt a number of novel crystal modifications are formed. Some of these novel intermediates are stable and thus possible to isolate and characterize. Others are too short-lived to characterize and still others are crystalline while in a damp and wet state, but are transformed into various amorphous forms upon drying and are as a consequence difficult to characterize. During the drying process these modifications may pass through a number of additional forms with less crystalline content. All crystal modifications are though obtainable by the present process.

The process of the present invention makes the best use of the novel crystal modifications and their properties by making it possible to produce esomeprazole sodium in a more effective and efficient way.

The present process is advantageous since it allows esomeprazole sodium salt to be prepared directly from the corresponding potassium salt in high yield and good quality using crystal modifications with good filtering properties. Additional merits are high reproducibility, good process ability including safety and the use of one main solvent system throughout the whole process, preferably including the oxidation step and the subsequent steps and manipulations. More preferably the same solvent system is used in the present invention as is used to prepare esomeprazole potassium salt.

The process of the present invention comprises essentially of the following steps:
i) Dissolving esomeprazole neutral form in a suitable solvent $S_1$;
ii) Adding an additional suitable solvent $S_2$;
iii) Adding about 1 molar eqvivalents of a sodium salt of a suitable base B.
iv) Allow esomeprazole sodium salt to crystallize and isolate the formed salt.

In one embodiment of the present invention esomeprazole neutral form is prepared from the corresponding esomeprazole potassium salt and more or less immediately taken through the subsequent steps defined above. If so, the esomeprazole potassium salt can be prepared by any of the methods described in the prior art and thereafter suspended in solvent $S_1$. The pH shall thereafter be adjusted to produce esomeprazole in its neutral form. This pH adjustment can be made by the addition of about 1 molar eqvivalents of a suitable acid HA, preferably as an aqueous solution. Examples of such acid HA comprises, but is not limited to, all mineral acids that forms a water-soluble potassium salt, e.g. hydrochloric acid and acetic acid. The aqueous phase is thereafter discarded and the organic phase is optionally washed with water or brine. Esomeprazole neutral form is now ready to be used, more or less immediately, in steps ii) to iv) defined above.

In another embodiment of the present invention esomeprazole neutral form is prepared from the corresponding esomeprazole magnesium salt and more or less immediately taken through the subsequent steps defined above.

In one embodiment of the present invention solvent $S_1$ is toluene.

In one embodiment of the present invention solvent $S_2$ is metanol.

In one embodiment of the present invention solvent $S_2$ is etanol.

In one embodiment of the present invention solvent $S_2$ is isopropylalkohol.

In one embodiment of the present invention base B is hydroxide.

In one embodiment of the present invention base B is added as an aqueous solution.

In one embodiment of the present invention the crystallization in step iv) is initiated by seeding.

In one embodiment of the present invention step iii) above is performed before step ii).

Esomeprazole sodium salts isolated in step iv) will be dependent on which solvent $S_2$ that was used. The isolated esomeprazole sodium salt is thereafter dried and during the drying process most of solvent $S_2$ is removed together with some additional water. The isolated esomeprazole sodium salts according to the Examples are crystalline while in a damp and wet state, but are transformed into various amorphous forms upon drying. During the drying process the isolated crystal modifications may pass through a number of additional forms with less crystalline content.

All esomeprazole sodium salts obtainable by the present process can be dried using conventional drying processes, as appropriate, to transform them into various amorphous forms. The drying procedure will slightly influence the position and intensities of the peaks in the X-ray diffractograms of esomeprazole sodium modification C, E and H. In order to fully reproduce the diffractograms of FIG. 1 to 3 it is important to carefully follow the procedure of the Examples. Slight deviations therefrom may influence the position and intensities of the peaks in the X-ray diffractograms The crystal modifications of the present invention are thus most useful as intermediates due to their good filtering properties. However, they can all be completely dried and formulated into a pharmaceutical composition to be used in patients in need thereof.

When methanol is used as solvent S2 then esomeprazole sodium salt modification C is the isolated crystal modification.

When ethanol is used as solvent S2 then esomeprazole sodium salt modification E is the isolated crystal modification.

When isopropylalkohol is used as solvent S2 then esomeprazole sodium salt modification H is the isolated crystal modification.

For the avoidance of doubt it is to be understood that where in this specification a process step or similar activities is qualified by "hereinbefore defined", "defined hereinbefore" or "defined above" the step encompasses the first occurring and broadest definition as well as each and all of the other definitions for that step.

The phrase "more or less immediately" as used in the present specification is to be understood to mean that the subsequent step or action shall be performed at such a time to avoid degradation of the active compound. This subsequent step can thus be performed considerably later in time provided that due care has been taken to avoid degradation of the active compound.

Suitable solvents $S_1$ comprises, but are not limited to, toluene.

Suitable solvents $S_2$ comprises, but are not limited to, methanol, ethanol and isopropylalkohol.

Suitable bases B comprises, but are not limited to, hydroxide, methoxide and ethoxide and are preferably added as an aqueous solution.

Another object of the present invention is to provide new stable crystal modifications of esoprazole sodium salt. Esomeprazole sodium salt can exist in more than one crystal modification. The crystal modifications or forms are hereinafter referred to as esomeprazole sodium salt modifications C, E, and H. The notation C, E, and H relates to the order in time in which the crystal modification were created, not to their relative thermodynamic stability.

It is an aspect of the present invention to provide esomeprazole sodium salt modification C.

Esomeprazole sodium salt modification C is characterized in providing an X-ray powder diffraction pattern, as in FIG. 1, exhibiting substantially the following main peaks with d-values and intensities;

| Modification C | |
|---|---|
| d-value (Å) | Relative intensity |
| 15.7 | vs |
| 7.9 | s |
| 6.1 | m |
| 5.3 | m |
| 4.56 | w |
| 3.59 | w |
| 3.49 | w |
| 3.17 | w |

The peaks, identified with d-values calculated from the Bragg formula and intensities, have been extracted from the diffractogram of esomeprazole sodium salt modification C. Only the main peaks, that are the most characteristic, significant, distinct and/or reproducible, have been tabulated, but additional peaks can be extracted, using conventional methods, from the diffractogram. The presence of these main peaks, reproducible and within the error limit, is for most circumstances sufficient to establish the presence of said crystal modification. The relative intensities are less reliable and instead of numerical values the following definitions are used;

| | |
|---|---|
| vs (very strong): | >15% rel int. |
| s (strong): | 7-15% rel int. |
| m (medium): | 3-7% rel int. |
| w (weak): | 1-3% rel int. |
| vw (very weak): | <1% rel int. |

* The relative intensities are derived from diffractograms measured with variable slits.

It is a further aspect of the present invention to provide esomeprazole sodium salt modification E.

Esomeprazole sodium salt modification E is characterized in providing an X-ray powder diffraction pattern, as in FIG. 3, exhibiting substantially the following d-values and intensities;

| Modification E | |
|---|---|
| d-value (Å) | Relative intensity |
| 15.5 | vs |
| 11.8 | w |
| 10.1 | w |
| 6.4 | w |

-continued

Modification E

| d-value (Å) | Relative intensity |
|---|---|
| 6.2 | m |
| 5.4 | w |
| 5.2 | m |
| 4.28 | w |
| 3.46 | w |
| 3.40 | w |
| 3.12 | w |

The peaks, identified with d-values calculated from the Bragg formula and intensities, have been extracted from the diffractogram of esomeprazole sodium salt modification E. Only the main peaks, that are the most characteristic, significant, distinct and/or reproducible, have been tabulated, but additional peaks can be extracted, using conventional methods, from the diffractogram. The presence of these main peaks, reproducible and within the error limit, is for most circumstances sufficient to establish the presence of said crystal modification. The relative intensities are less reliable and instead of numerical values the following definitions are used;

| | |
|---|---|
| vs (very strong): | >15% rel int. |
| s (strong): | 8-15% rel int. |
| m (medium): | 5-8% rel int. |
| w (weak): | 1-5% rel int. |
| vw (very weak): | <1% rel int. |

\* The relative intensities are derived from diffractograms measured with variable slits.

It is a further aspect of the present invention to provide Esomeprazole sodium salt modification H.

Esomeprazole sodium salt modification H is characterized in providing an X-ray powder diffraction pattern, as in FIG. 5, exhibiting substantially the following d-values and intensities;

Modification H

| d-value (Å) | Relative intensity |
|---|---|
| 22.0 | vs |
| 18.1 | w |
| 11.1 | m |
| 6.3 | w |
| 5.7 | m |
| 5.3 | m |
| 4.92 | s |
| 4.56 | m |
| 3.73 | m |

The peaks, identified with d-values calculated from the Bragg formula and intensities, have been extracted from the diffractogram of esomeprazole sodium salt modification H. Only the main peaks, that are the most characteristic, significant, distinct and/or reproducible, have been tabulated, but additional peaks can be extracted, using conventional methods, from the diffractogram. The presence of these main peaks, reproducible and within the error limit, is for most circumstances sufficient to establish the presence of said crystal modification. The relative intensities are less reliable and instead of numerical values the following definitions are used;

| | |
|---|---|
| vs (very strong): | >50% rel int. |
| s (strong): | 27-50% rel int. |
| m (medium): | 11-27% rel int. |
| w (weak): | 3-11% rel int. |
| vw (very weak): | <3% rel int. |

\* The relative intensities are derived from diffractograms measured with variable slits.

Crystallization of crystal modifications of the present invention from an appropriate solvent system, containing a plurality of solvents, may be achieved by attaining supersaturation in a solvent system by solvent evaporation, by temperature decrease, and/or via the addition of anti-solvent (i.e. a solvent in which the crystal modifications are poorly soluble).

Whether an hydrate or solvate crystallizes is related to the kinetics and equilibrium conditions of the respective crystal modification at the specific condition. Thus, as may be appreciated by the skilled person, the crystal modification that is obtained depends upon both the kinetics and the thermodynamics of the crystallization process. Under certain thermodynamic conditions (solvent system, temperature, pressure and concentration of compound of the invention), one crystal modification may be more stable than another (or indeed any other). However, crystal modifications that have a relatively low thermodynamic stability may be kinetically favored. Thus, in addition, kinetic factors, such as time, impurity profile, agitation, the presence or absence of seeds, etc. may also influence which crystal modification that crystallizes.

In order to ensure that a particular crystal modification is prepared in the substantial absence of other crystal modifications, crystallization is preferably carried out by seeding with seed crystals of the desired crystal modification. This applies particularly to each of the specific crystal modifications which are described in the Examples.

Esomeprazole sodium salt modification C, E, and H obtainable according to the present invention is substantially free from other crystal and non-crystal forms of esomeprazole sodium salt. The term "substantially free from other crystal and non-crystal forms of esomeprazole sodium salt form" shall be understood to mean that the desired crystal form of esomeprazole sodium salt contains less than 15%, preferably less than 10%, more preferably less than 5% of any other forms of esomeprazole sodium salt form.

The crystal modifications of the present invention are effective as a gastric acid secretion inhibitor, and are thus useful as antiulcer agents. In a more general sense, they can be used for prevention and treatment of gastric-acid related conditions in mammals and especially in man, including e.g. reflux esophagitis, gastritis, duodenitis, gastric ulcer and duodenal ulcer. Furthermore, they may be used for treatment of other gastroihtestinal disorders where gastric acid inhibitory effect is desirable e.g. in patients on NSAID therapy, in patients with Non Ulcer Dyspepsia, in patients with symptomatic gastro-esophageal reflux disease, and in patients with gastrinomas. They may also be used in patients in intensive care situations, in patients with acute upper gastrointestinal bleeding, pre- and postoperatively to prevent aspiration of gastric acid, to prevent and treat stress ulceration and asthma, and for improvement of sleep. Further, the crystal modifications of the invention may be useful in the treatment of psoriasis as well as in the treatment of Helicobacter infections and related diseases. The crystal modifications of the invention may also be used for treatment of inflammatory conditions in mammals, including man.

Any suitable route of administration may be employed for providing the patient with an effective dosage of the crystal modifications. For example, peroral or parenteral formulations, including i.v., and the like may be employed. Dosage forms include capsules, tablets, dispersions, suspensions, solutions and the like.

It is further provided a pharmaceutical composition comprising the crystal modifications of the present invention, as active ingredient, in association with a pharmaceutically acceptable carrier, diluent or excipient and optionally other active pharmaceutical ingredients. Compositions comprising other therapeutic ingredients are of interest in the treatment of the conditions listed above. The invention also provides the use of the crystal modifications in the manufacture of a medicament for use in said conditions as well as a method of treating a gastric-acid related condition which method comprises administering to a subject suffering from said condition a pharmaceutically effective amount of the crystal modifications.

The compositions of the invention includes compositions suitable for peroral, i.v. or parenteral administration. The most preferred route is the i.v. route. The compositions may be conveniently presented in unit dosage forms, and prepared by any methods known in the art of galenic pharmacy.

In the practice of the invention, the most suitable route of administration as well as the magnitude of the therapeutic dose will depend on the nature and severity of the disease to be treated. The dose, and dose frequency, may also vary according to the age, body weight and response of the individual patient. Special requirements may be needed for patients having Zollinger-Ellison syndrome, such as a need for higher doses than the average patient. Children and patients with liver diseases generally will benefit from doses that are somewhat lower than average. Thus, in some conditions it may be necessary to use doses outside the ranges stated below, for example long-term treatments may request lower dosage. Such higher and lower doses are within the scope of the present invention. Such daily doses may vary between 5 mg to 300 mg.

In general, a suitable oral dosage form of the compound of the invention may cover a dose range from 5 mg to 300 mg total daily dose, administered in one single dose or equally divided doses. A preferred dosage range is from 10 mg to 80 mg.

The compound of the invention may be combined as the active component in intimate admixture with a pharmaceutical carrier according to conventional techniques, such as the oral formulations described in WO 96/01623 and EP 0 247 983, the disclosures of which are hereby as a whole included by reference.

Combination preparations comprising the compounds of the invention and other active ingredients may also be used. Examples of such active ingredients include, but are not limited to anti-bacterial compounds, non-steroidal anti-inflammatory agents, antacid agents, alginates and prokinetic agents.

The compounds of the invention may be further processed before formulation into a suitable pharmaceutical formulation. For example, the crystal modification may be milled or ground into smaller particles.

For the avoidance of doubt, "treatment" includes the therapeutic treatment, as well as the prophylaxis, of a condition.

The presence of additional substances in a sample, like pharmaceutical excipients, to be characterised by X-ray powder diffraction can of course mask some of the small peaks in any of the above characterized crystal modifications. This fact alone can of course not demonstrate that the crystal modification is not present in the sample. Under such circumstances due care must be used and the presence of substantially all main peaks in the X-ray powder diffraction pattern might suffice to characterize the crystal modification. It is thus preferred to analyse the crystal modifications of the present invention without the presence of additional substances.

The invention is illustrated, but in no way limited, by the following examples.

EXAMPLES

General Procedures

X-ray powder diffraction analysis (XRPD) was performed on samples prepared according to standard methods, for example those described in Giacovazzo, C. et al (1995), Fundamentals of Crystallography, Oxford University Press; Jenkins, R. and Snyder, R. L. (1996), Introduction to X-Ray Powder Diffractometry, John Wiley & Sons, New York; Bunn, C. W. (1948), Chemical Crystallography, Clarendon Press, London; or Klug, H. P. & Alexander, L. E. (1974), X-ray Diffraction Procedures, John Wiley and Sons, New York. X-ray diffraction analyses were performed using a Philips X'Pert MPD for 16 minutes from 1 to 40° 2θ. The samples were analyzed without internal reference since the addition may affect the time spent on preparation of the sample and thus influence the position and intensities of the peaks in the X-ray diffractograms. Measured peak values have been adjusted based on previous experiences (−0.05° 2θ). Calculation into d-values was done thereafter.

XRPD distance values may vary in the range ±2 on the last given decimal place.

Example 1.1

Preparation of Esomeprazole Sodium Salt Modification C

Esomeprazole-K (11.89 g) was dissolved in water (50 ml) and toluene (80 ml) was added. Then, the pH was adjusted to approximately 7 by adding acetic acid (5.89 ml, 25% v/v). The two phases were mixed for 10 minutes and then allowed to separate. The water phase was removed and the remaining organic phase was washed with aqueous NaCl-solution (50 ml, 10%). After phase separation, methanol (4.24 ml) was added to the toluene phase and, then 1 eq NaOH (1.52 ml, aq, 45%) was added. The solution was seeded with 25 mg Eso-Na. The crystallisation was left over night with stirring, the crystals were filtered off by vacuum filtration and quickly washed twice with toluene (2×10 ml). The resulting wet filter cake was dried shortly, e.g 2-5 minutes, in air before the analysis.

Example 1.2

Preparation of Esomeprazole Sodium Salt Modification E

Esomeprazole-K (11.89 g) was dissolved in water (50 ml) and toluene (80 ml) was added. Then, the pH was adjusted to approximately 7 by adding acetic acid (5.89 ml, 25% v/v). The two phases were mixed for 10 minutes and then allowed to separate. The water phase was removed and the remaining organic phase was washed with aqueous NaCl-solution (50 ml, 10%). After phase separation, ethanol (11.1 ml) was added to the toluene phase and, then 1 eq NaOH (1.52 ml, aq, 45%) was added. The solution was seeded with 55 mg Eso-Na. The crystallisation was left over night with stirring, the crystals were filtered off by vacuum filtration and quickly washed twice with toluene (2×10 ml). The resulting wet filter cake was dried shortly, e.g 2-5 minutes, in air before the analysis.

Example 1.3

Preparation of Esomeprazole Sodium Salt Modification H

Esomeprazole-K (11.89 g) was dissolved in water (50 ml) and toluene (80 ml) was added. Then, the pH was adjusted to approximately 7 by adding acetic acid (5.89 ml, 25% v/v). The two phases were mixed for 10 minutes and then allowed to separate. The water phase was removed and the remaining organic phase was washed with aqueous NaCl-solution (50 ml, 10%). After phase separation, 2-propanol (3.6 ml) was added to the toluene phase and, then 1 eq NaOH (1.52 ml, aq, 45%) was added. The solution was seeded with 53 mg Eso-Na. The crystallisation was left over night with stirring, the crystals were filtered off by vacuum filtration and quickly washed twice with toluene (2×10 ml). The resulting wet filter cake was dried shortly, e.g 2-5 minutes, in air before the analysis.

The invention claimed is:

1. A process for preparing esomeprazole sodium salt modification C, the process comprising the steps of:
   i) suspending esomeprazole potassium salt in toluene and adjusting the pH by adding about 1 molar equivalent of hydrochloric acid or acetic acid as an aqueous solution thereby forming a toluene phase and an aqueous phase;
   ii) separating the phases and adding to the separated toluene phase a solvent consisting of methanol;
   iii) adding to the solution formed in step ii) about 1 molar equivalent of a sodium salt of a base B as an aqueous solution;
   iv) allowing esomeprazole sodium salt modification C to crystallize; and
   v) isolating the formed esomeprazole sodium salt modification C.

2. The process according to claim 1, wherein the base B is hydroxide.

3. The process according to claim 1, wherein crystallization of step iv) is initiated by seeding.

4. Esomeprazole sodium salt modification C, wherein the salt has an X-ray powder diffraction pattern having peaks expressed in d-values at 15.7, 7.9, 6.1, 5.3, 4.56, 3.59, 3.49, 3.17 Å.

5. Esomeprazole sodium salt modification C, wherein the salt has an X-ray powder diffraction pattern substantially as shown in FIG. 1.

6. A process for preparing esomeprazole salt modification C, the process comprising the steps of:
   i) dissolving esomeprazole potassium salt in water, adding toluene and adjusting the pH to approximately 7 by adding acetic acid as an aqueous solution to form a toluene phase and an aqueous phase;
   ii) separating the toluene phase from the aqueous phase and washing the separated toluene phase with aqueous sodium chloride;
   iii) adding to the separated toluene phase a solvent consisting of methanol;
   iv) adding 1 molar equivalent sodium hydroxide as an aqueous solution;
   v) allowing esomeprazole sodium modification C to crystallize after seeding with esomeprazole sodium; and
   vi) isolating the formed esomeprazole sodium modification C after filtering.

7. Esomeprazole sodium salt modification C prepared by the process of claim 1, 2 or 6.

* * * * *